(12) United States Patent
Purdy et al.

(10) Patent No.: US 8,858,478 B2
(45) Date of Patent: Oct. 14, 2014

(54) METHOD AND SYSTEM FOR FLUIDIZED LOWER LEG PROTECTION

(76) Inventors: William Purdy, White Plains, NY (US); Robert Purdy, Bedord, NY (US)

(*) Notice: Subject to any disclaimer, the term of this patent is extended or adjusted under 35 U.S.C. 154(b) by 0 days.

(21) Appl. No.: 13/493,550

(22) Filed: Jun. 11, 2012

(65) Prior Publication Data

US 2013/0239976 A1      Sep. 19, 2013

Related U.S. Application Data

(60) Provisional application No. 61/614,782, filed on Mar. 23, 2012, provisional application No. 61/495,082, filed on Jun. 9, 2011.

(51) Int. Cl.
*A61F 5/00* (2006.01)

(52) U.S. Cl.
USPC ..................................... 602/13; 128/DIG. 20

(58) Field of Classification Search
CPC ............ A61K 2300/00; A61K 31/201; A61K 31/202; A61K 31/232; A61K 31/366; A61K 31/401; A61K 31/505; A61K 35/60; A61K 36/185; A61K 36/31; A61K 36/48; A61K 36/55; A61K 31/40; A61K 35/12; A61G 13/12; A61G 13/1245; A61G 13/125; A61G 13/1265; A61G 15/12; A61G 7/0755; A61H 9/0078; A61H 2201/1642; A61H 2201/1676; A61H 1/0274; A61H 2201/0103; A61H 2201/0149; A61H 2201/165; A61H 1/0266; A61H 2201/5002; A61H 1/0237; A61H 2201/5056; A61H 2201/5074; A61F 7/02; A61F 2007/0054; A61F 2007/0056; A61F 7/007; A61F 7/106; A61F 2007/0001; A61F 2007/023; A61F 5/32; A61F 5/34; A61F 9/0008; A61F 2007/003; A61F 2007/0032; A61F 2007/0042
USPC ........ 602/13, 16, 20–27, 60–63; 128/DIG. 20
See application file for complete search history.

(56) References Cited

U.S. PATENT DOCUMENTS

| | | | |
|---|---|---|---|
| 5,328,445 A * | 7/1994 | Spahn et al. ..................... | 602/13 |
| 5,423,333 A * | 6/1995 | Jensen et al. .................. | 128/878 |
| 5,895,366 A * | 4/1999 | Bzoch .............................. | 602/24 |
| 8,216,165 B2 * | 7/2012 | Ravikumar et al. ............. | 602/13 |
| 2003/0139695 A1 * | 7/2003 | Riach .............................. | 602/13 |
| 2012/0253250 A1 | 10/2012 | Spahn et al. | |

* cited by examiner

*Primary Examiner* — Michael A. Brown
(74) *Attorney, Agent, or Firm* — Porzio, Bromberg & Newman, P.C.

(57) ABSTRACT

The present invention relates to a fluidized lower leg protection and support system and method. The system can include an inner positioner. The inner positioner can displace and contour three-dimensionally as though it was fluid to the sides and top of the leg while not having flow characteristics that would result in migration of the medium under the force of gravity. The system can also include an outer support which is received over the inner positioner. The outer support can be in the shape of an open boot. The outer support can include an ultra low pressure plenum. The ultra low pressure plenum is filled at a predetermined low pressure for distributing pressure along the length of the outer support, but not providing significant elevation of the lower leg and heel by itself.

23 Claims, 22 Drawing Sheets

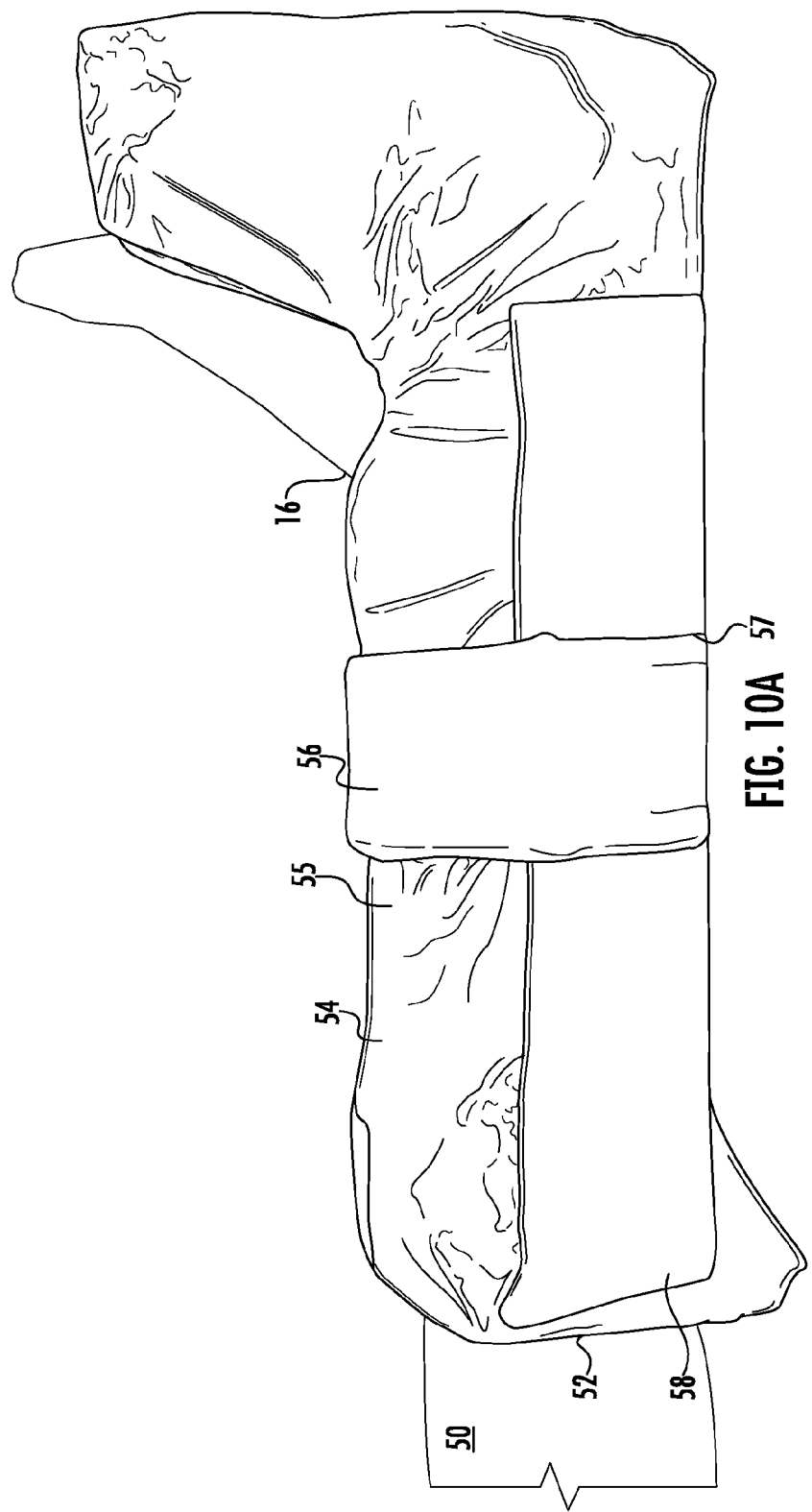

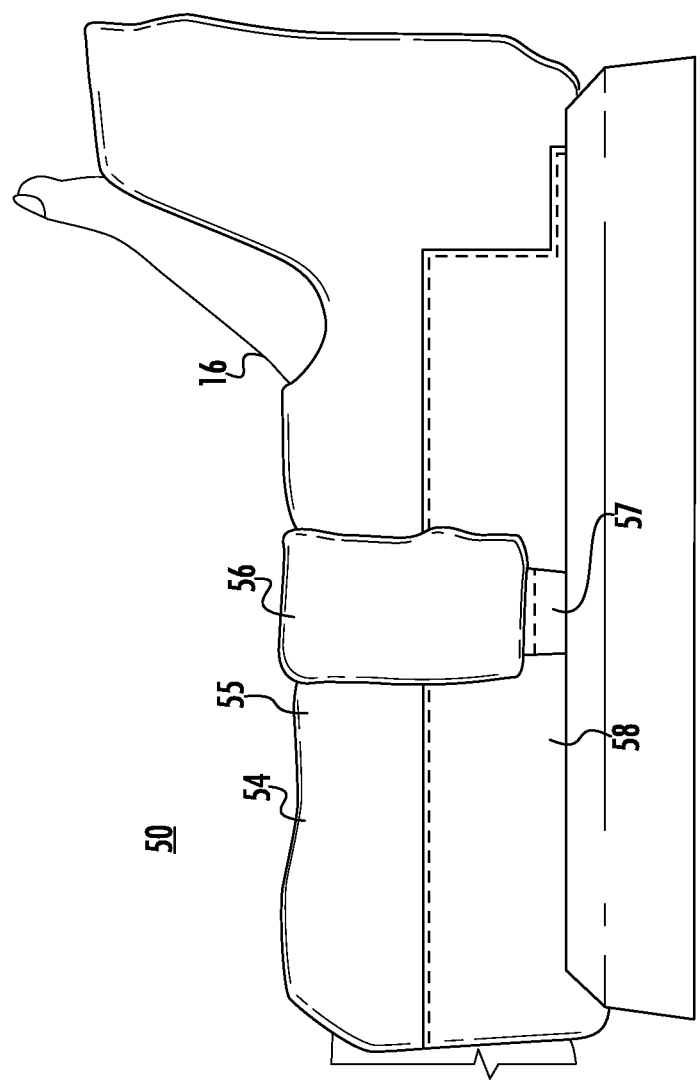

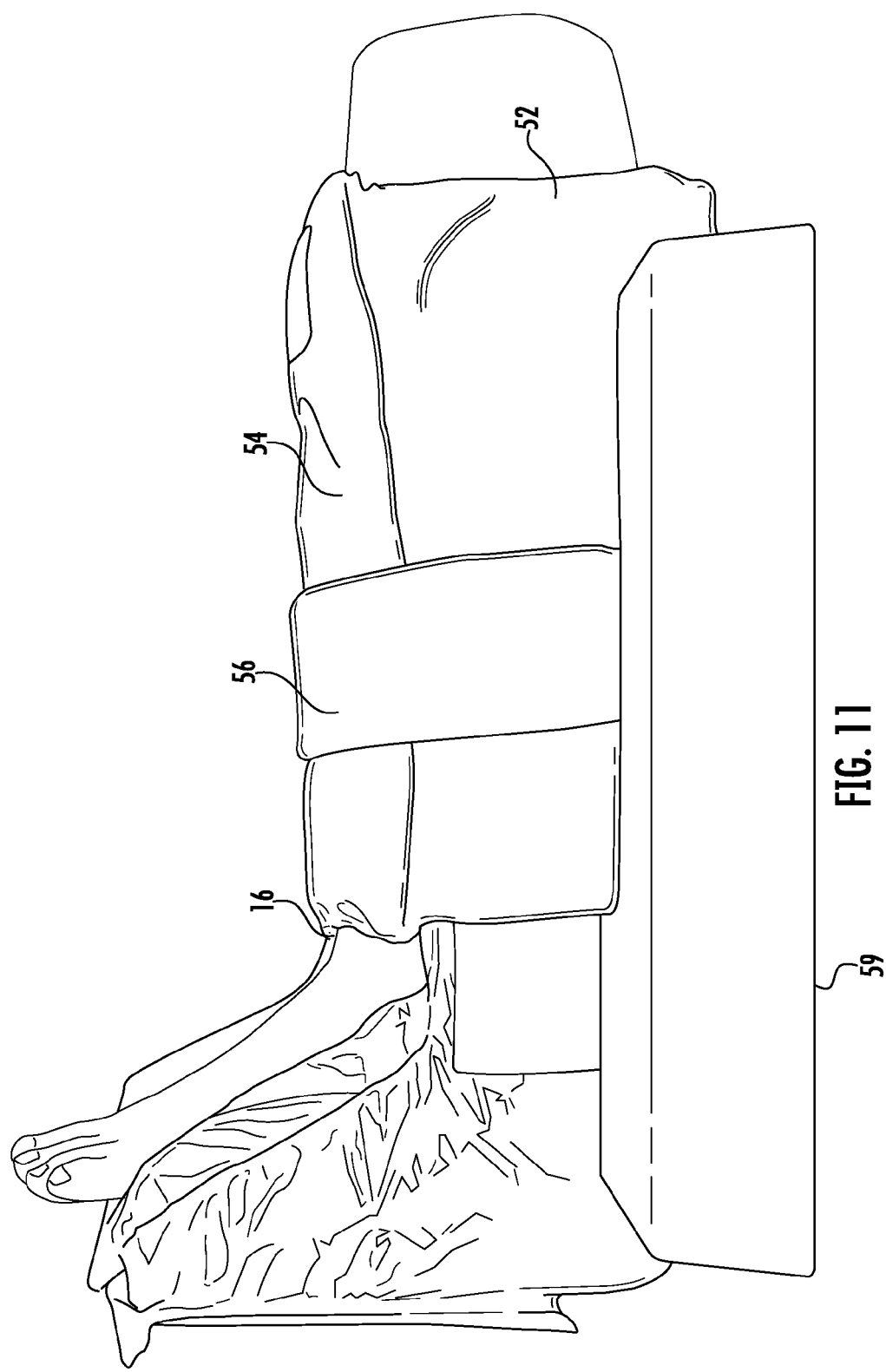

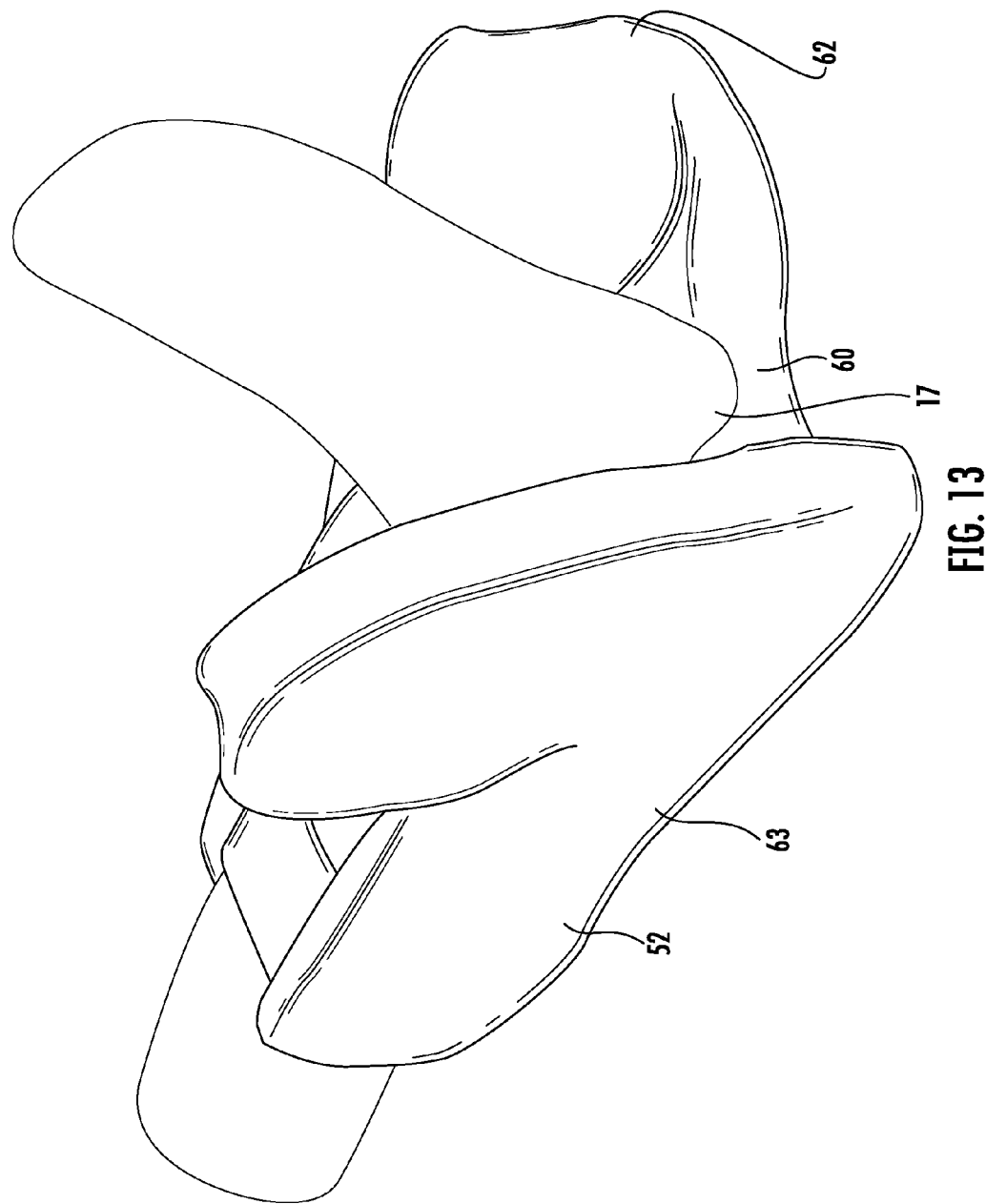

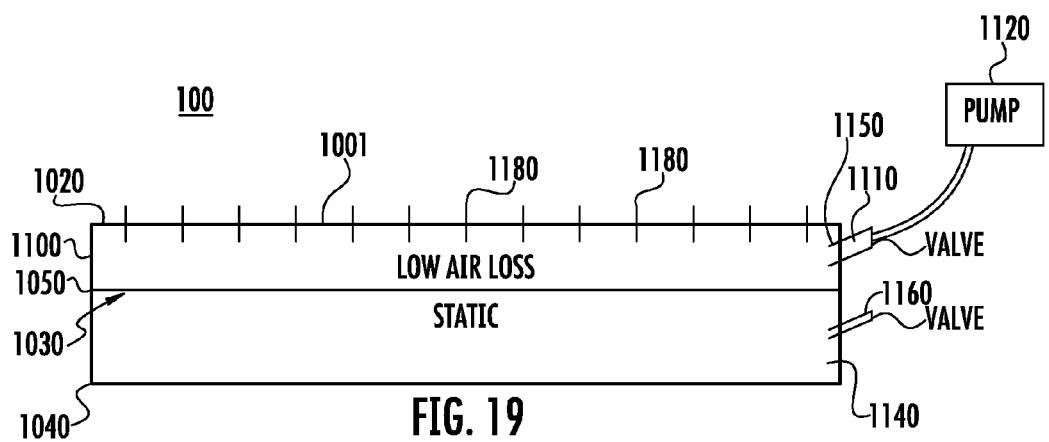

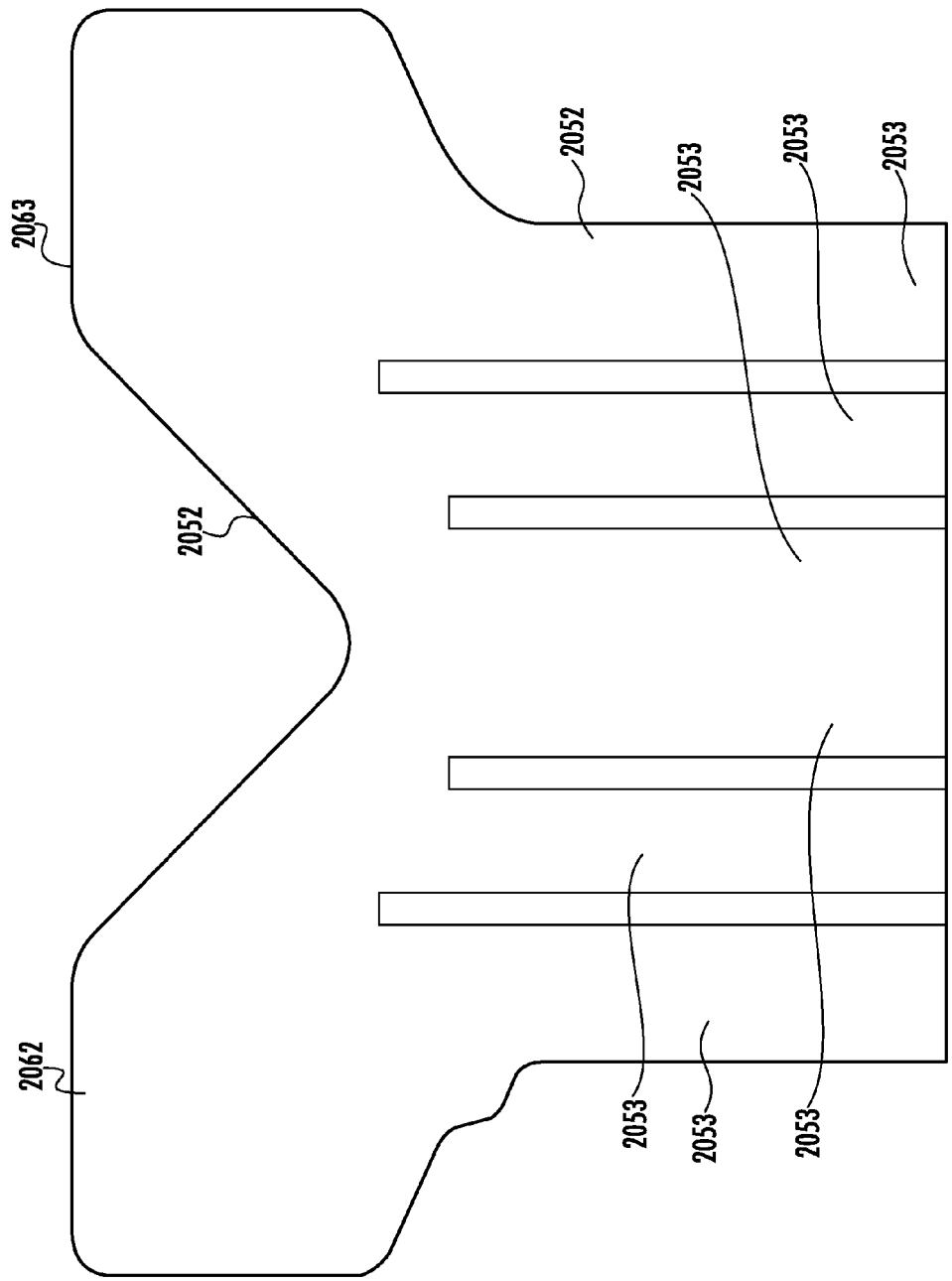

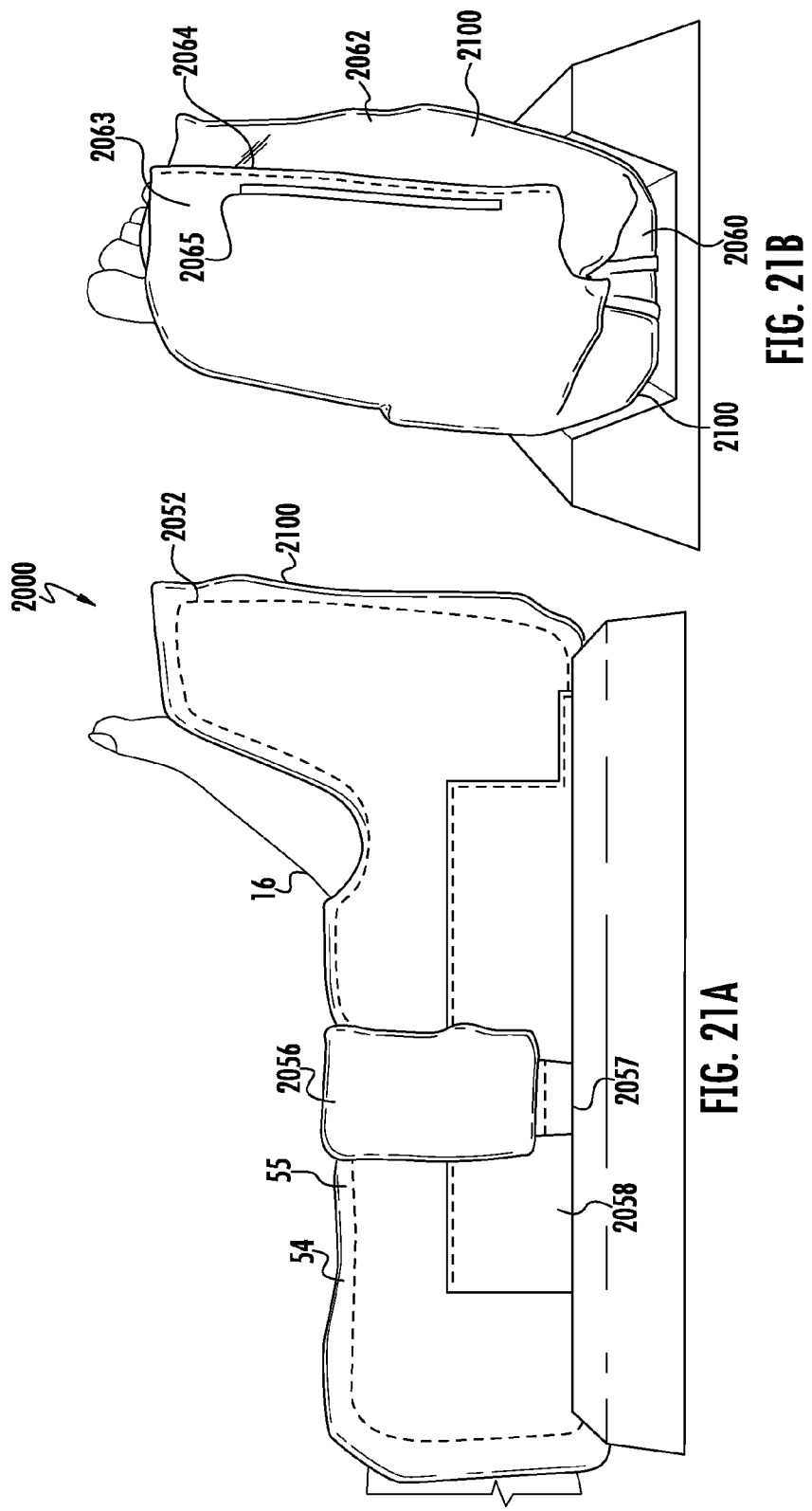

METHOD AND SYSTEM FOR FLUIDIZED LOWER LEG PROTECTION

CROSS REFERENCE TO RELATED APPLICATION

This application claims the benefit of U.S. Provisional Patent Application No. 61/614,782 filed Mar. 23, 2012 and U.S. Provisional Patent Application No. 61/495,082, filed Jun. 9, 2011, the entireties of which applications are hereby incorporated by reference into this application.

BACKGROUND OF THE INVENTION

Conventional supports provide a polyester filled or foam boot for support of a lower leg. Other conventional supports include an ankle foot orthotic (AFO) or foot wrap. Another conventional support includes an air chamber in a boot configuration. The air chamber supports a leg and heel above a surface of a bed patient when lying in a supine or side lying position, such as in a hospital bed. The conventional supports have the disadvantage that pressure is applied to the heel or leg for maintaining the heel above the surface of the bed. In addition, the leg can be raised too high such that joints can lock, nerves can be potentially entrapped and the circulation to the leg can be compromised. In addition, the intralumenal pressure of conventional supports minimizes its ability to contour to the object applying the force.

It is desirable to provide a low pressure fluidized lower leg protection system for supporting the leg and heel when a patient is recumbent while maintaining neutral leg alignment without lifting the leg and heel from the resting surface.

SUMMARY OF THE INVENTION

The present invention relates to a fluidized lower leg protection and support system and method. It is optimal to barely elevate the heel from the surface of the bed. This helps to minimize leg rotation and locking of the knee. The system can include an inner positioner. The inner positioner includes a bladder preferably filled with a fluidized particulate material to provide three-dimensional contouring to the lower leg and heel. The inner positioner has low pressure and is not sufficient alone to support the leg. The inner positioner has little or no flow characteristics unless an outside force is applied other than gravity. The inner positioner can displace and contour three-dimensionally as though it was fluid to the sides and top of the leg while not having flow characteristics that would result in migration of the medium under the force of gravity. The inner positioner can provide three-dimensional contouring to the Achilles tendon. The inner positioner can include a temperature regulating material for keeping the leg in an optimal range of skin temperature to keep the leg comfortable longer. The inner positioner can be shaped as a pad to mold to the underside portion of the lower leg and heel. Alternatively, the inner positioner can include various shapes to support the lower leg and heel. In one embodiment, the inner positioner also includes a portion which extends over a top portion of the leg (shin).

The system can also include an outer support which is received over the inner positioner. The outer support can be in the shape of an open boot. The outer support can include an ultra low pressure plenum. The ultra low pressure plenum is filled at a predetermined low pressure for distributing pressure along the length of the outer support, but not providing significant elevation of the lower leg and heel by itself. The ultra low pressure plenum will not support the lower leg and heel unless the ultra low outer support is closed around the lower leg and heel. In this embodiment, the inner positioner is partially filled with the fluidized particulate material so it cannot support a leg on its own. For example, the inner positioner can be filled up to ⅔ of its capacity. The inner support provides three-dimensional contouring to the supported lower leg and heel. The outer portion of the inner positioner contours to the inner portion of the ultra low pressure plenum for providing more gas displacement of the outer support than if the inner positioner was not present.

In one embodiment the system is strapless. In an alternate embodiment, the system includes a strap for attachment of the outer support to the leg. The strap can be sufficiently wide and cushioned to protect the skin. In one embodiment, the strap is air bearing. In one embodiment, a rear end of the outer support includes a gate, which can be opened to allow access to the foot and heel from the rear of the boot. When the outer support is fully opened, the outer support is in a flat position to provide a treatment area without lifting of the leg.

The inner positioner or outer support can include a fluidized thermal regulating medium. In one embodiment, a phase change material can be used for adjusting the temperature of the system.

The system of the present invention can be a one size fits all and adapts to the size and shape of a patient's leg. The system maintains neutral alignment and helps prevent foot drop. The system gently but securely wraps the leg, helping to maintain constant heel position. The system promotes proper dorsiflexion without causing undue pressure on the lower limb.

The combination of the inner positioner including a fluidized medium along with the outer support including a ultra low pressure plenum creates sufficient support of the lower leg while responding to normal patient movement. The combination of the inner positioner and the outer support provides three-dimensional contouring to the lower leg and heel for micro adjustment while the outer support or boot is closed for minimizing friction and shear. This is not possible in conventional devices having the disadvantage that the inner chamber is not free to communicate with the leg without negatively affecting the functionality of the outer chamber. In general, the custom fitting protection can be used in such a way as to elevate the foot without "locking out the knee" due to three-dimensional molding and provide comfort to the skin. The natural contour of the leg can be maintained while eliminating harmful pressure to the heel, ankle, Achilles and foot. The system of the present invention can respond to the twisting of the leg without causing movement of the outer support. The system of the present invention can minimize shear forces that would be associated with a non-fluidized medium.

The invention will be more fully described by reference to the following drawings.

BRIEF DESCRIPTION OF THE DRAWINGS

FIG. 10A is a schematic diagram of an alternate embodiment of a fluidized lower leg protection and support system including an outer support.

FIG. 10B is a schematic diagram of an alternate embodiment of a fluidized lower leg protection and support system including an outer support.

FIG. 11 is a schematic diagram of the embodiment of a fluidized lower leg protection and support system shown in FIG. 10 from an opposite side.

FIG. 13 is a schematic diagram of the embodiment of a fluidized lower leg protection and support system shown in FIG. 10 from a rear side in an open position.

FIG. 19 is a schematic diagram of an alternate embodiment of a fluidized lower leg protection and support system including a plenum providing low air loss.

FIG. 21A is a schematic diagram of an alternate embodiment of a fluidized leg protection and support system including a cover.

FIG. 21B is a schematic diagram of a rear view of the fluidized leg protection and support system shown in FIG. 21A.

FIG. 20 is a schematic diagram of plan view of an outer support used in the fluidized leg protection and support system.

DETAILED DESCRIPTION

Figure 1:
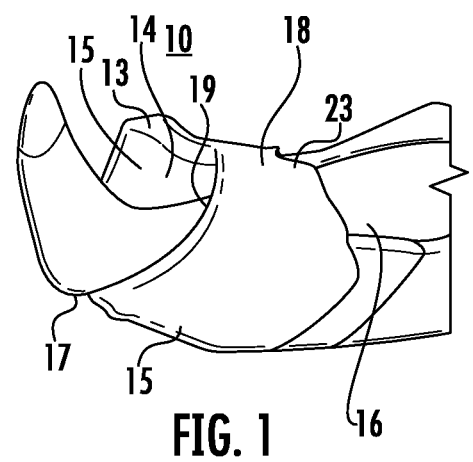
FIG. 1 is a schematic diagram of an inner support of a fluidized lower leg protection and support system.

Reference will now be made in greater detail to a preferred embodiment of the invention, an example of which is illustrated in the accompanying drawings. Wherever possible, the same reference numerals will be used throughout the drawings and the description to refer to the same or like parts.

Fluidized lower leg protection and support system 10 includes inner positioner 14, as shown in FIG. 1. Inner positioner 14 is formed of bladder 13 including fluidized material 15 therein. Fluidized material 15 can be a particulate material including interstitial spaces between the particles. A lubricant can be present in the interstitial spaces. For example, the lubricant can be a particulate material having a lower coefficient of friction, such as a powder. The volume of the particulate material can be controlled for controlling the interstitial air within the fluidized medium.

Bladder 13 is filled with fluidized material 15 which can retain its shape after sculpting. The flowability or lubricity of fluidized material 15 can be increased by adding a lubricant or by the removal of gas from the interstitial spaces or both. The preferred medium of fluidized material 15 is a particulate material that has been modified in such a way that it acts like a fluid Fluidized material 15 refers to a compound or composition which can be sculpted and retain its shape and has no memory or substantially no memory. The no memory or substantially no memory feature enables bladder 13 to increase in height and maintain support of a body part. Fluidized material 15 is made of a viscosity that will allow it to contour but not collapse under the weight of the body part.

At sea level, the normal interstitial air pressure would exceed about 760 millibars of mercury. This increases or decreases marginally as altitude varies. Depending on the nature of the particulate fluidized material 15, the pressure can be lowered below about 500 millibars, preferably, lowered below about 350 millibars to about 5 millibars, while still maintaining the necessary flow characteristics of the product. The amount the pressure is lowered is dependent on the interstitial spaces needed to provide desired flow characteristics of the product.

Fluidized material 15 can include beads, such as polyethylene or polystyrene (PS) beads, expanded polyethylene (PE), crosslinked expanded polyethylene (PE), polypropylene (PP) pellets, closed cell foams, microspheres, encapsulated phase changing materials (PCM). The beads can be hard shelled or flexible. In one embodiment, the beads are flexible and gas can be evacuated from the beads. In one embodiment, hard beads can be mixed with flexible beads in which gas can be evacuated from the flexible beads. In an alternative embodiment, fluidized material 15 can a porous foam substance including pockets of interstitial gas. In one embodiment, fluidized material 15 can be a polyurethane foam. The polyurethane foam can be open or closed cell and cut into small shapes such as spheres or blocks. For example, a sphere of polyurethane foam can have a size of 2 inches in diameter. For example, a block of polyurethane foam can be a 1×1×1 inch block.

Suitable examples of fluidized material 15 can be formed of a mixture of microspheres and lubricant. The microspheres can include hollow or gas-filled structural bubbles (typically of glass or plastic) with an average diameter of less than about 200 microns. The composition flows and stresses in response to a deforming pressure exerted on it and the composition ceases to flow and stresses when the deforming pressure is terminated. For example, fluidized material 15 can be formed of a product referenced to as Floam™. A flowable compound comprising lubricated microspheres, including the compound itself, formulations for making the compound, methods for making the compound, products made from the compound and methods for making products from the compound as defined by U.S. Pat. Nos. 5,421,874, 5,549,743, 5,626,657, 6,020,055, 6,197,099 and 8,171,585, each of which is hereby incorporated by reference into this application. Bladder 13 provides micro-contouring because fluidized material 15 can respond three dimensionally.

For example, bladder 13 can be formed of a flexible plastic, such as urethane. Upon removal of residual gas from fluidized material 15 bladder 13 flows concurrent with the flow of fluidized material 15 such that bladder 13 moves with movement of fluidized material 15. Bladder 13 can have a size and shape to support lower leg 16 and heel 17 of a user. Bladder 13 can include portion 18 which extends over top portion 19 of lower leg 16. Optionally, gas can communicate throughout the whole bladder 13 for allowing maximum contouring and functional displacement of both the gas and the fluidized chamber thereby providing maximum contouring to a desired body part.

Figure 2:
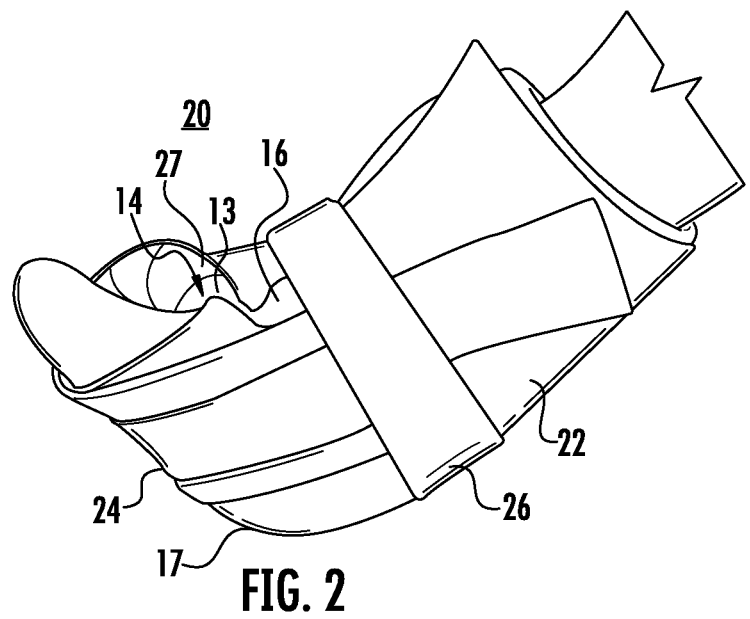
FIG. 2 is a schematic diagram of an embodiment of the fluidized lower leg protection and support system including an outer support.
Figure 3:
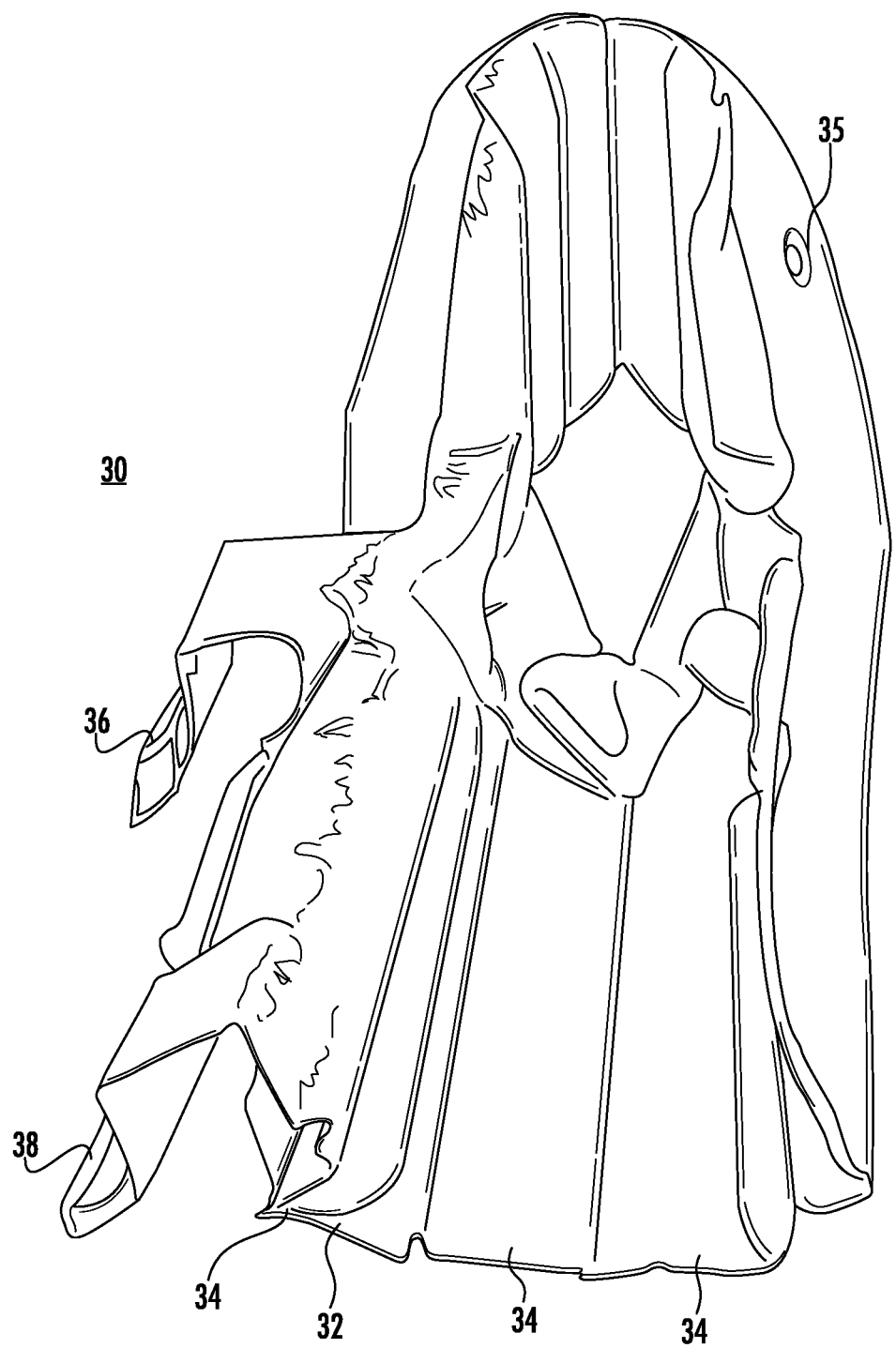
FIG. 3 is a schematic diagram of an alternate embodiment of the fluidized lower leg protection and support system including an outer support.

FIG. 2 is a schematic diagram of an embodiment of fluidized lower leg protection and support system 20 including outer support 22. Outer support 22 is configured in a shape to conform to a shape of lower leg 16 and optionally heel 17. Outer support 22 can include ultra low pressure plenum 24 within outer support 22. Air pressure within ultra low pressure plenum 24 is reduced sufficiently to provide reduced pressure for conforming outer support 22 to the shape of lower leg 16 and optionally heel 17 for distributing pressure along the length of outer support 22. Lower pressure plenum 24 does not provide support of lower leg 16 and heel 17. For example, the pressure in ultra low pressure plenum 24 can be below 20 mm of water. It will be appreciated that all equivalents such as mm Hg and PSI can be used for measuring the pressure within ultra low pressure plenum 24.

The pressure within ultra low pressure plenum 24 can be below about 20 mm of water if no inner positioner is used or if an area of less than about 30% of outer support 22 is covered by inner positioner 14. The pressure within ultra low pressure plenum 24 can be below about 10 mm of water if an area of between about 30% to about 60% of outer support 22 is covered by inner positioner 14. The pressure within ultra low pressure plenum 24 can be below about 5 mm of water if an area of greater than about 60% of outer support 22 is covered by inner positioner 14.

Outer support 22 can be received over inner positioner 14. Inner positioner 14 can be shaped as a pad to mold to the underside portion of lower leg 16 and heel 17. Inner positioner 14 is formed of bladder 13 including fluidized material 15 therein which can retain its shape after sculpting, as described above.

Strap 26 can be attached to outer support 22. Strap 26 can include a hook and loop material for attaching outer support to lower leg 16. Strap 26 can have a width in the range of one to five inches which is comfortable to the user. Strap 26 can include a cushioning material. In one embodiment, strap 26 is air bearing.

Inner positioner 14 or outer support 22 can include thermo-regulating medium 27. Thermo-regulating medium 27 can be a phase change material for adjusting the temperature to adapt support system 10 to temperature changes of a body part of a user. Thermo-regulating material 27 can be associated with fluidized material 15 or cover (not shown) placed over inner positioner 14. An example material for thermo-regulating material 27 is manufactured by Outlast Technologies as fibers, fabrics, and foams comprising micro-encapsulated phase changing materials referred to as Thermocules, which store and release heat as further described in U.S. Pat. Nos. 7,790,283, 7,666,502 and 7,579,078, hereby incorporated by reference into this application.

FIG. 3-FIG. 9 illustrate alternate embodiments of an embodiment of fluidized lower leg protection and support system 30 including outer support 32. Outer support 32 includes a plurality of continuous ultra low pressure plenums 34. A gas can be added at a predetermined pressure through valve 35 for inflating side ultra low pressure plenums 34.

Figure 4:
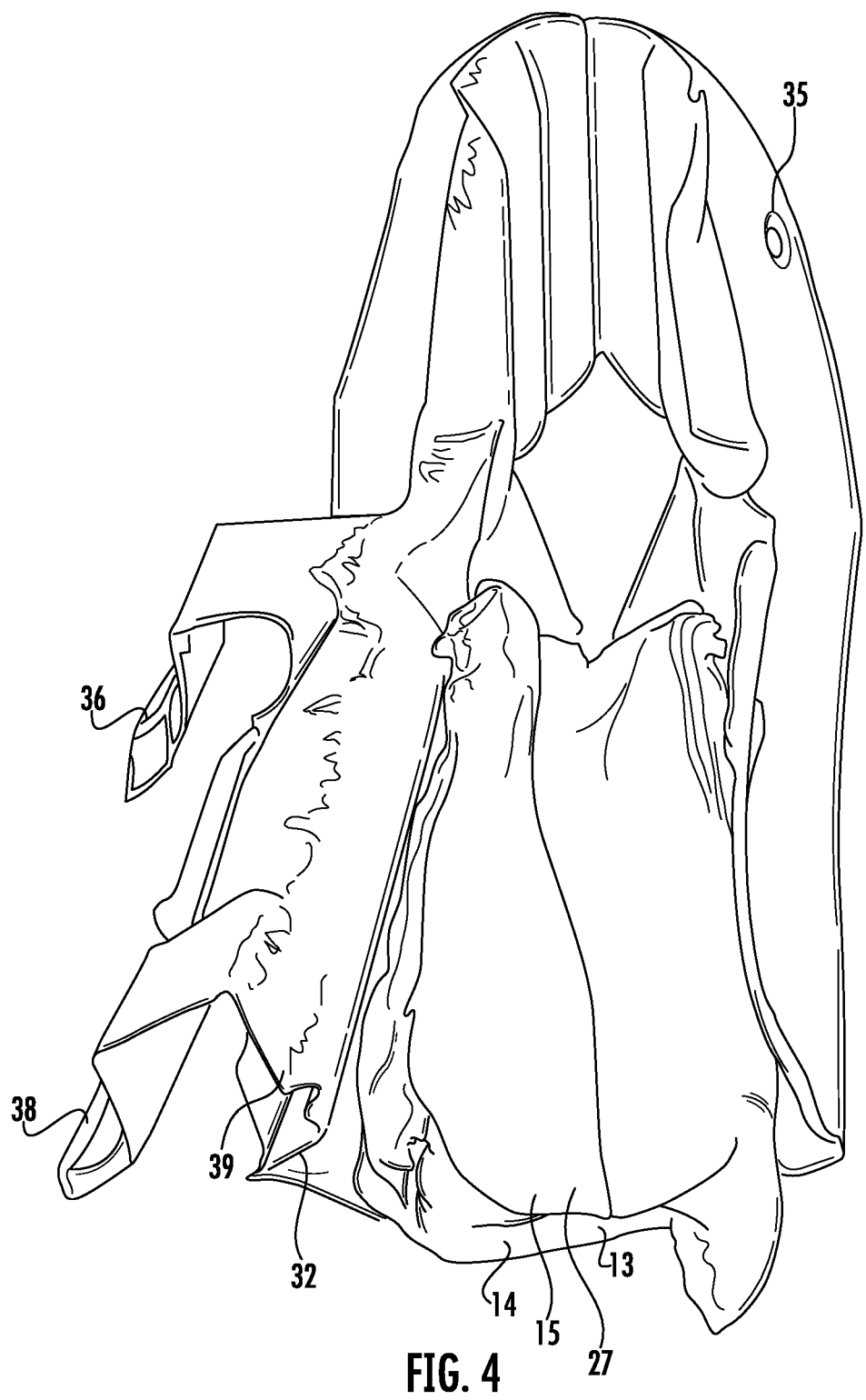
FIG. 4 is a schematic diagram of the outer support for the system shown in FIG. 3.
Figure 5:
FIG. 5 is a schematic diagram of an alternate embodiment of the fluidized lower leg protection and support system including an outer support.
Figure 6:
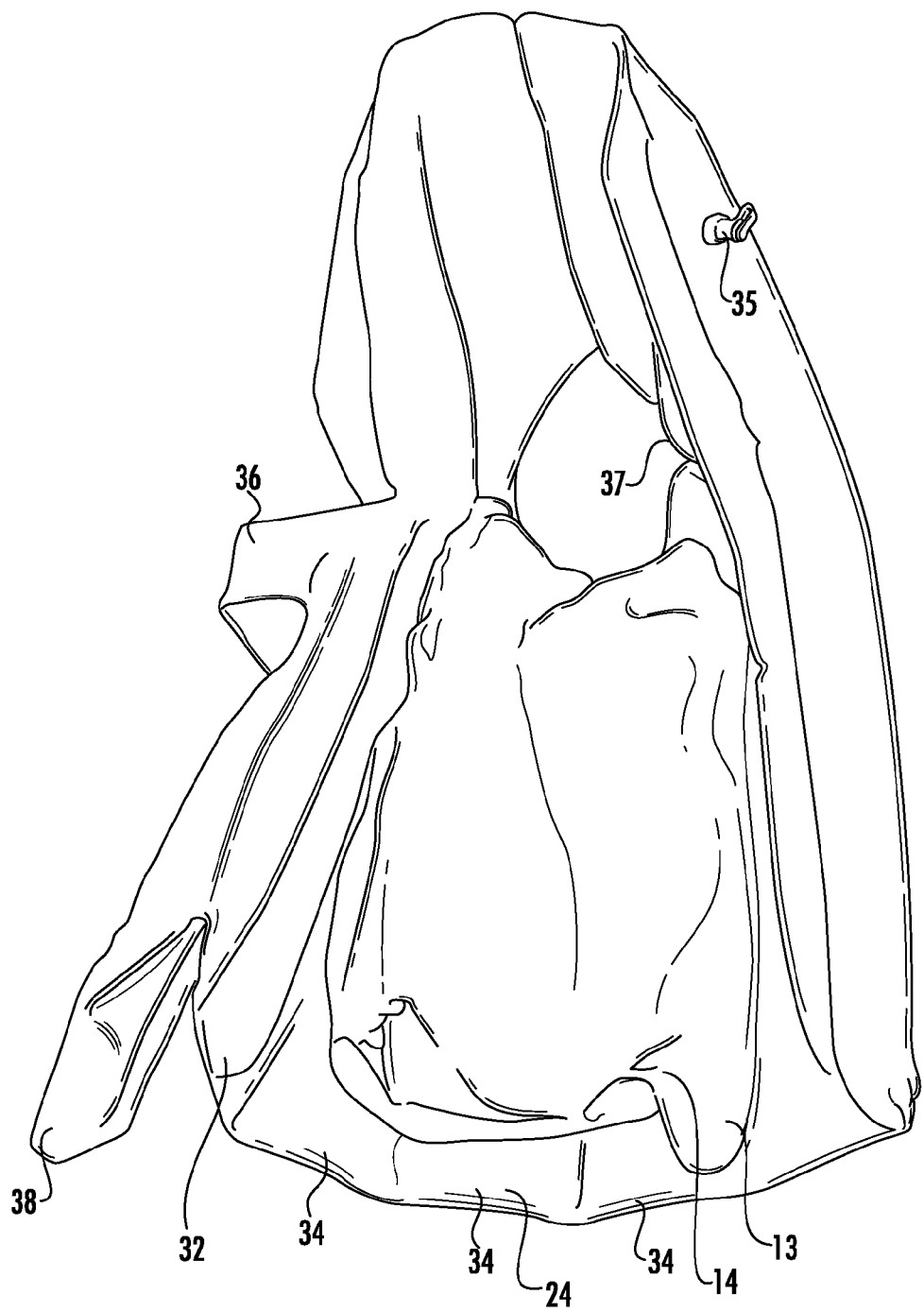
FIG. 6 is a schematic diagram of the outer support for the system shown in FIG. 5.
Figure 7:
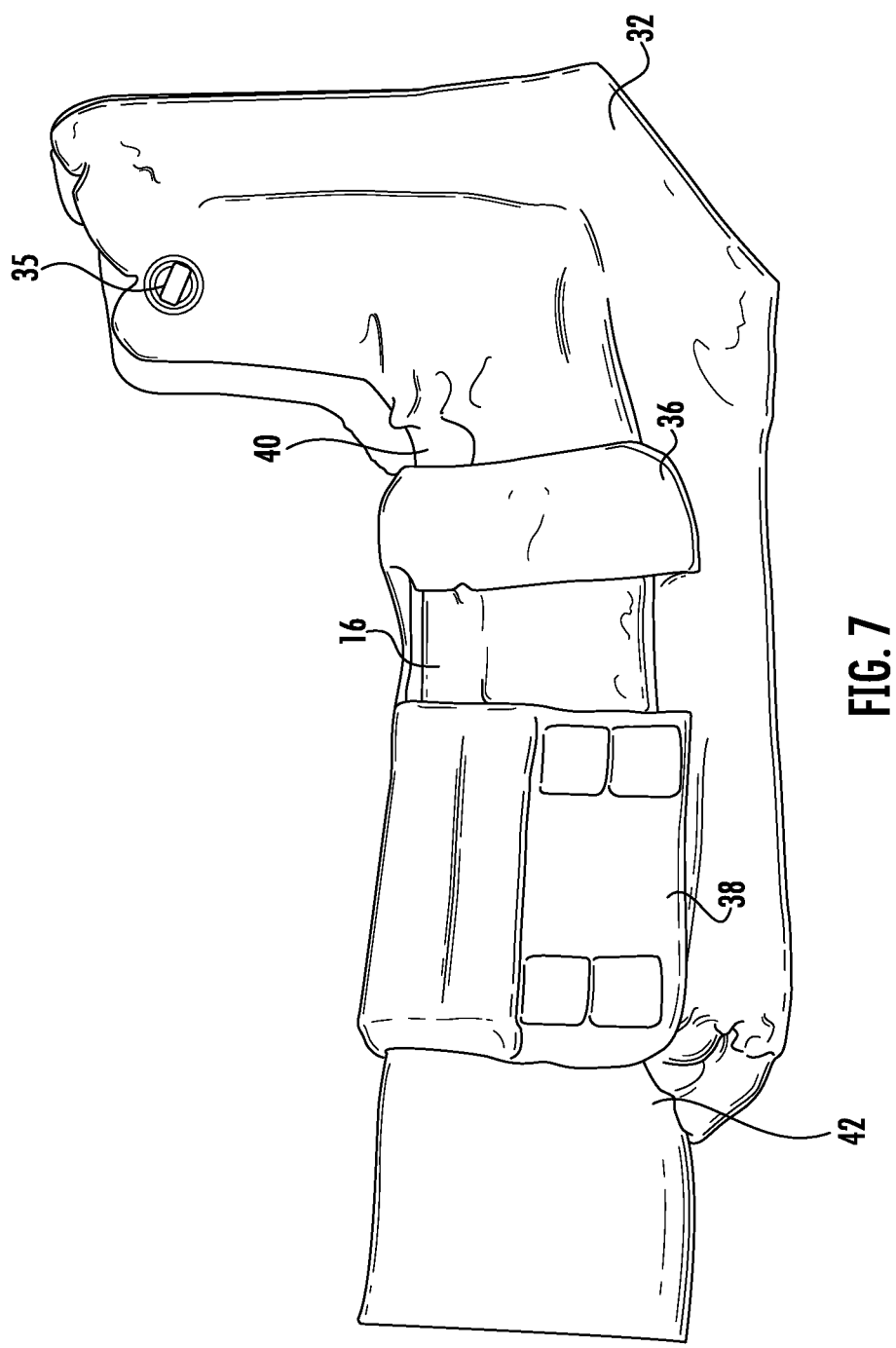
FIG. 7 is a schematic diagram of the system of FIG. 5 in a closed position.
Figure 8:
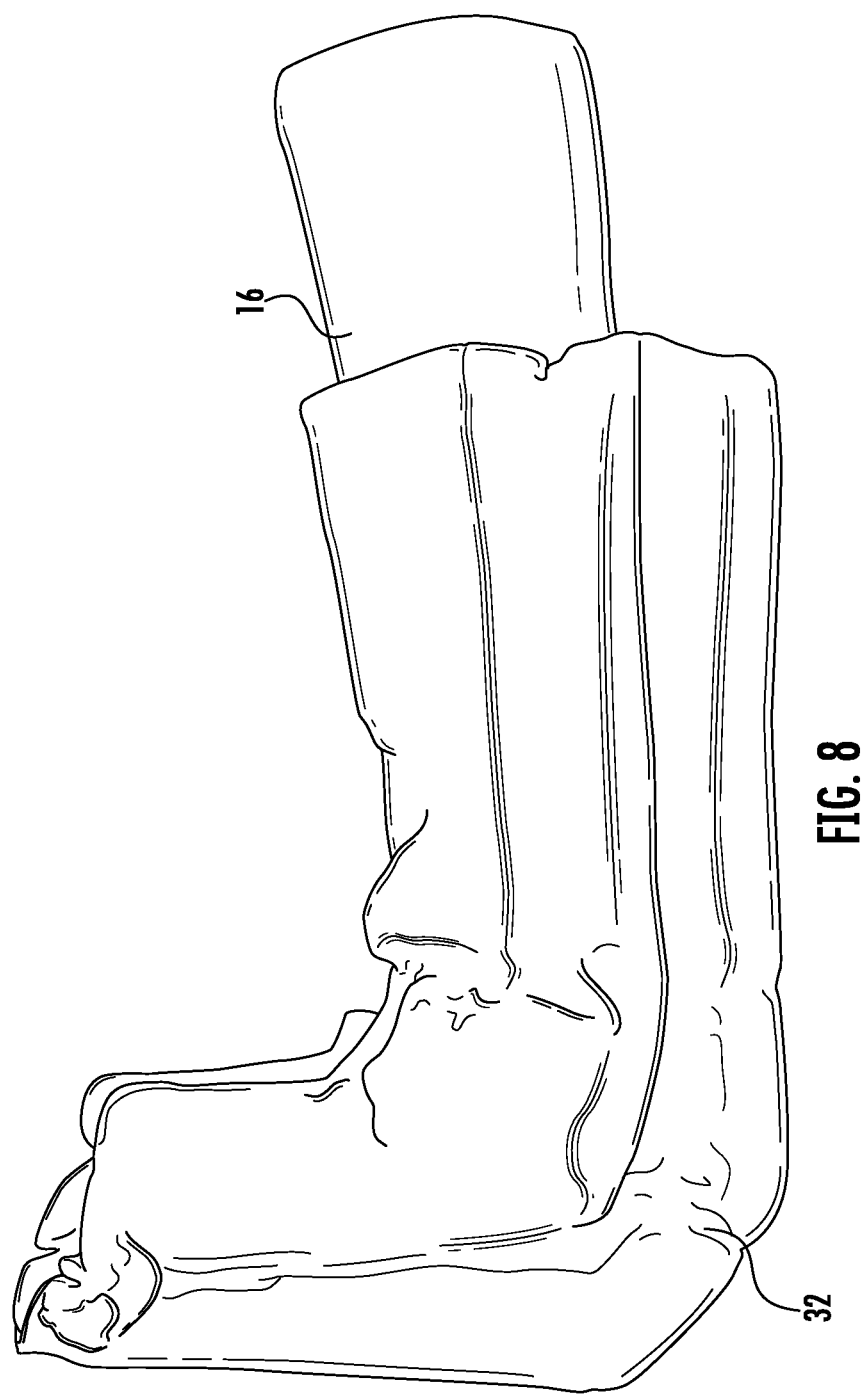
FIG. 8 is a schematic diagram of the other side of the diagram shown in FIG. 7.
Figure 9:
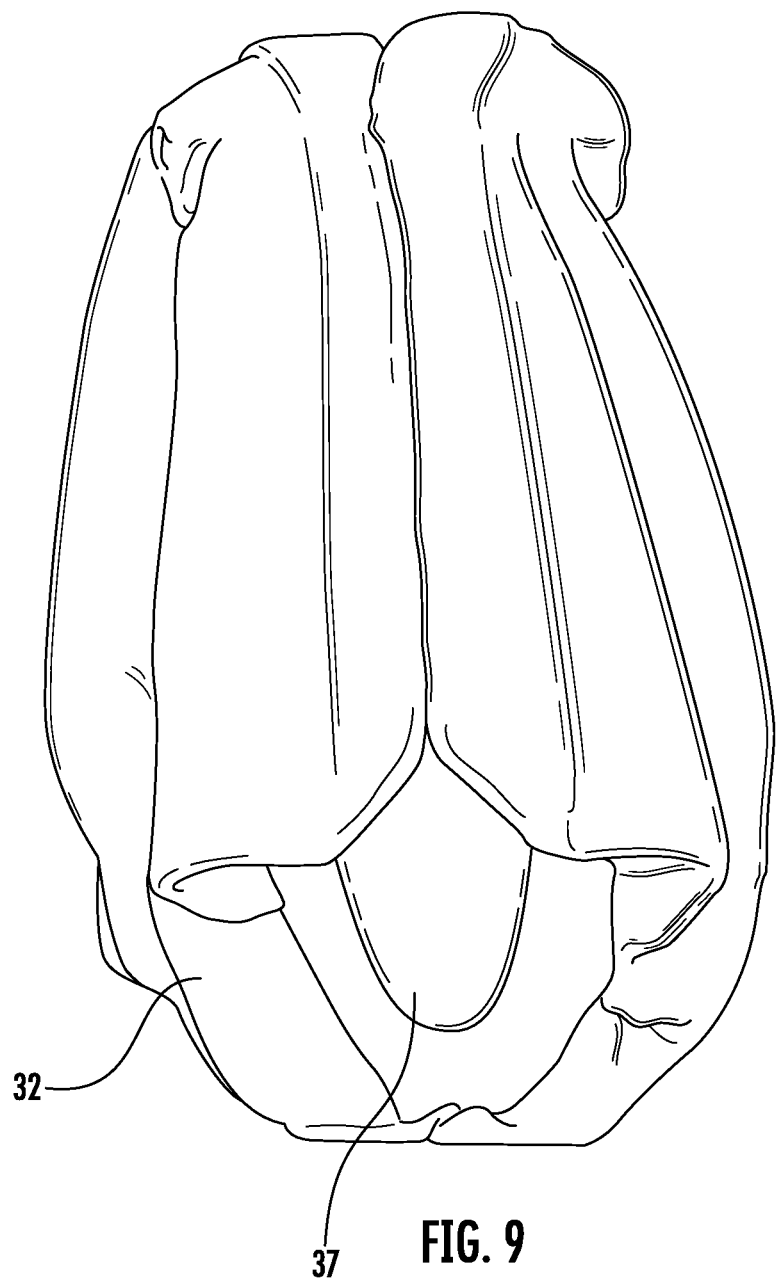
FIG. 9 is an end view of the diagram shown in FIG. 7.

Straps 36 and 38 extend from side 39 of outer support 32 for closing outer support 32 around lower leg 16, as shown in FIGS. 7 and 8. Straps 36 and 38 can be air bearing. Strap 36 can provide closure near ankle 40. Strap 38 can provide closure around calf 42. Preferably, strap 38 has a wider diameter, for example, in the range of about 3 inches to about 5 inches for providing closure around calf 42. Inner positioner 14 formed of bladder 13, including fluidized material 15 is received within outer support 32, as shown in FIGS. 4 and 6. Bottom end of outer support 32 can include opening 37, as shown in FIG. 9. During use, inner diameter 50 of bladder 13 contours to lower leg 16 and heel 17 and outer diameter 52 of bladder 13 contours to outer support 32.

Figure 12A:
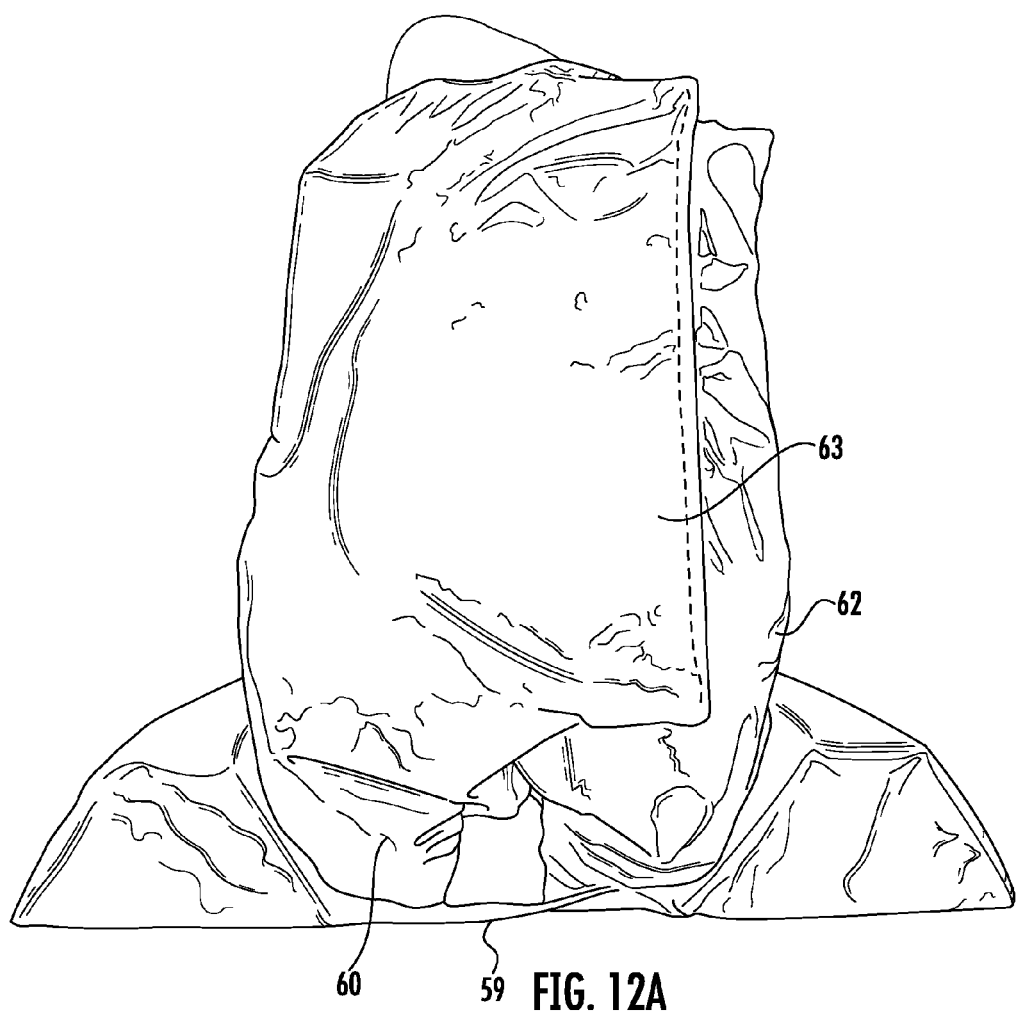
FIG. 12A is a schematic diagram of the embodiment of a fluidized lower leg protection and support system shown in FIG. 10 from a rear side.
Figure 12B:
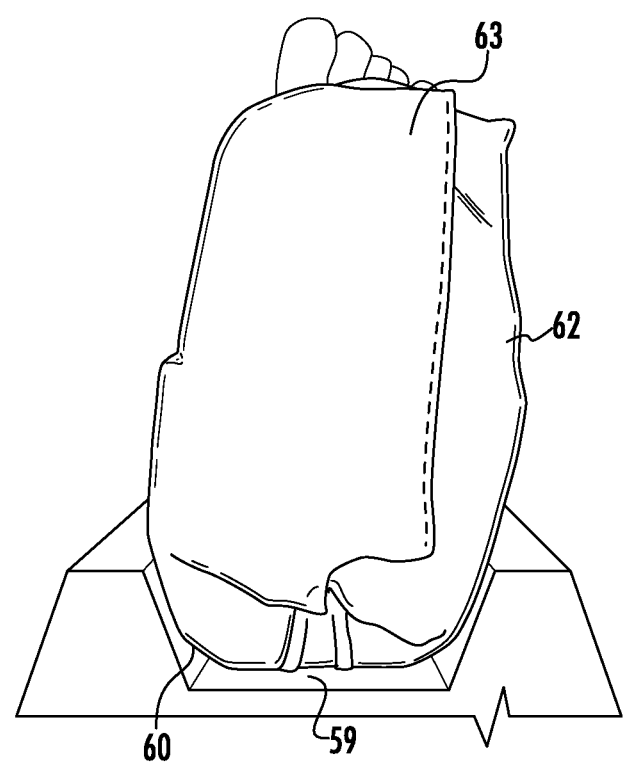
FIG. 12B is a schematic diagram of the embodiment of a fluidized lower leg protection and support system shown in FIG. 10 from a rear side.

FIGS. 10-14 illustrate an alternate embodiment of a fluidized lower leg protection and support system 50. Outer support 52 can include a plurality of rows of parallel ultra low pressure plenums 53. For example, ultra low pressure plenums 53 can be positioned within outer support 52 along the length $L_1$ of outer support 52. Flap 54 can extend over front of lower leg 16. Flap 54 can include air chambers 55, which protect lower leg 16 from strap 56. Flap 54 can also provide anti-rotation of fluidized lower leg protection and support system 50. Strap 56 can be adjustable for closing flap 54 for different sizes of legs. Strap 54 can include a coupling portion 57 at one end thereof for attaching to attachment section 58. Coupling portion 57 can be formed of a hook and loop material. Attachment section 58 can be formed of a hook and loop material. Attachment section 58 can be positioned along length $L_1$ of outer support 52. Outer support 52 can be received under U-shaped base 59, as shown in FIG. 12. U-shaped base 59 provides anti-rotation of outer support 52.

Figure 14:
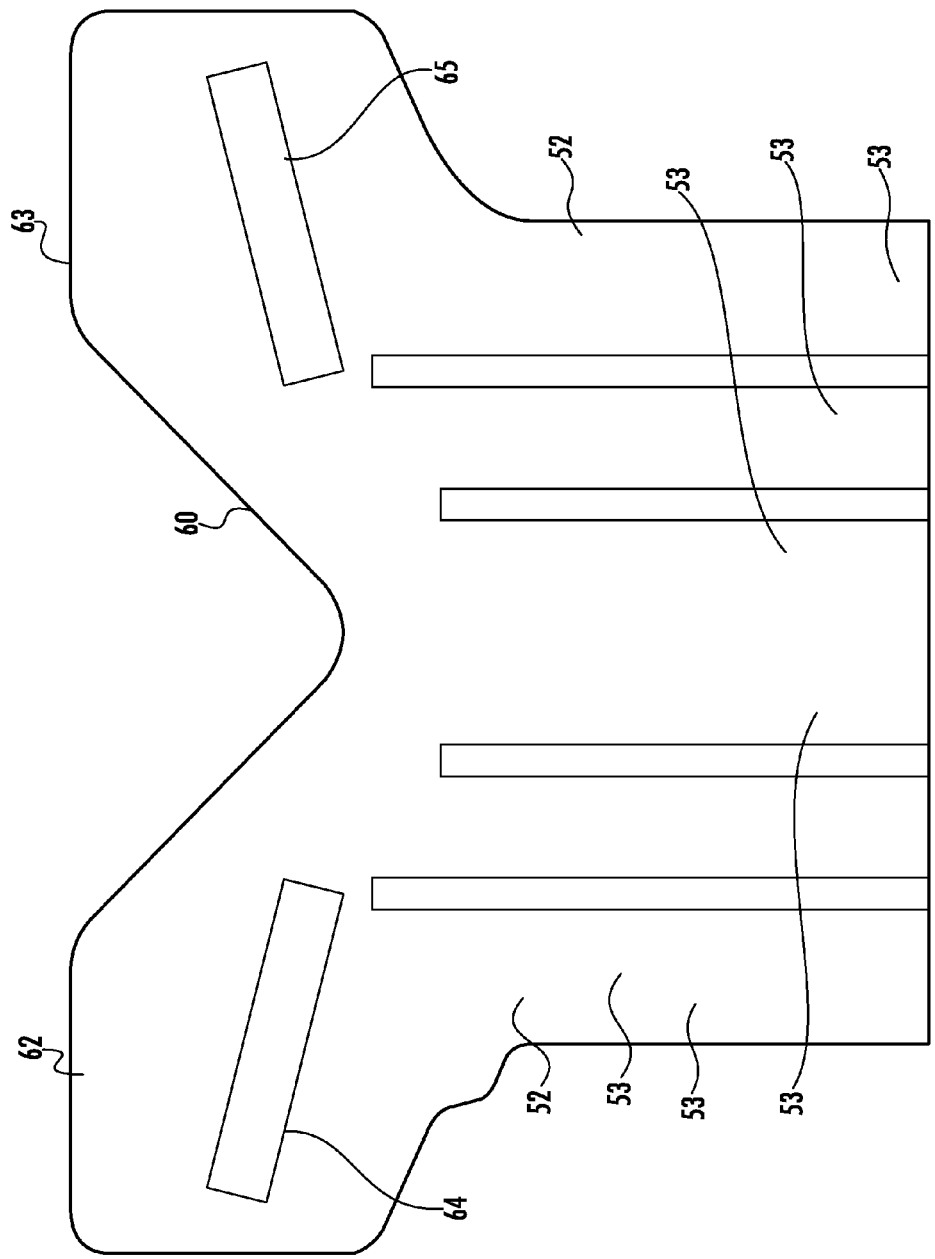
FIG. 14 is a schematic plan view of the embodiment of a fluidized lower leg protection and support system shown in FIG. 10.

Rear end 60 of outer support 52 can include overlapping flap members 62 and 63 for forming a gate to allow access to foot 19 including heel 17, as shown in FIGS. 12 and 13. Flap members 62 and 63 can include respective coupling portions 64 and 65 for attaching flap members 62 and 63 to one another. For example, coupling portions 64 and 65 can be formed of a hook and loop material. Flap members 62 and 63 can be opened to allow access to foot 19, as shown in FIG. 14.

Figure 15:
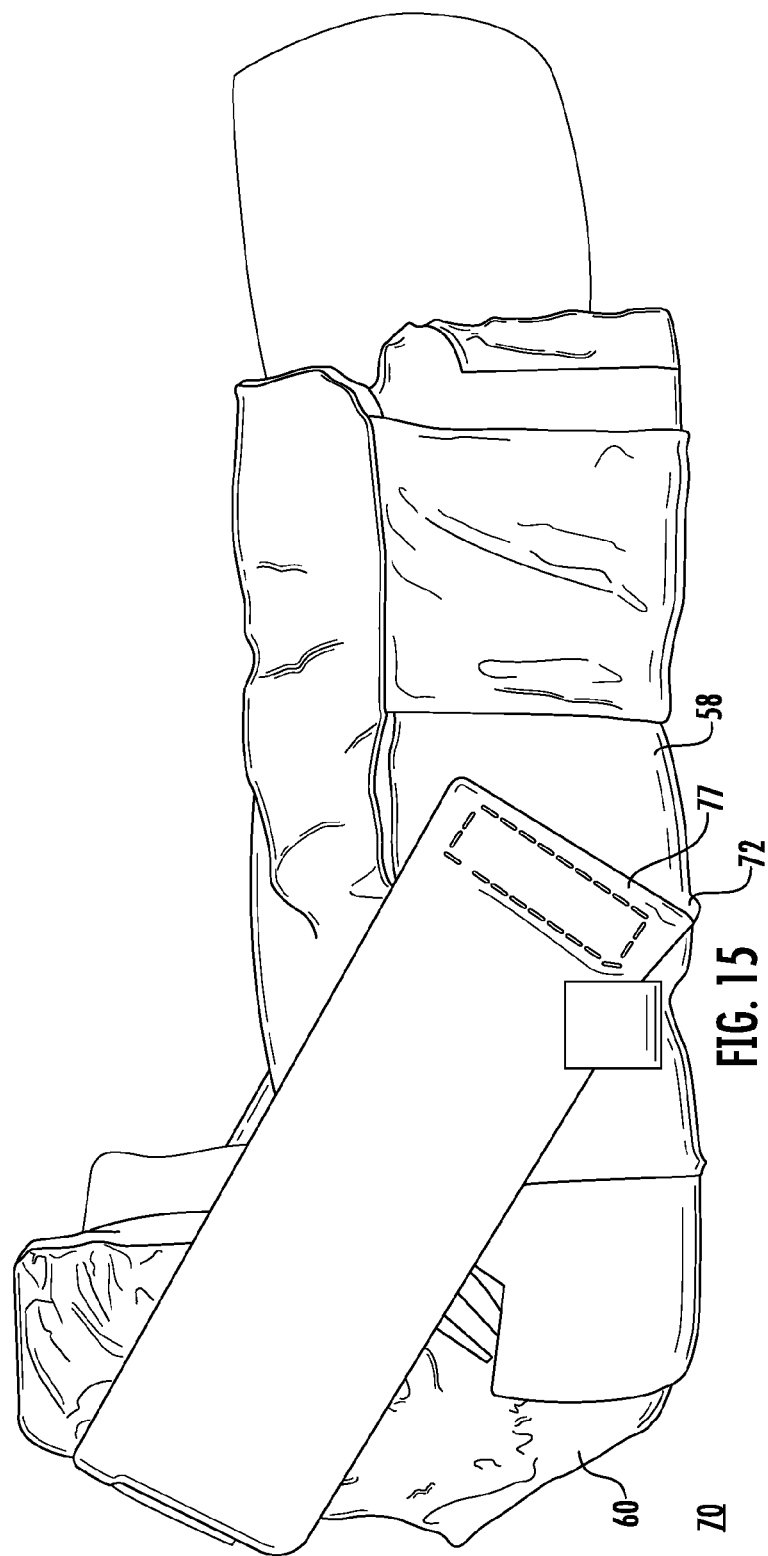
FIG. 15 is a schematic diagram of an alternate embodiment of a fluidized lower leg protection and support system including an outer support and support strap.

FIG. 15 illustrates an alternate embodiment of a fluidized lower leg protection support system 70, including support strap 72. Support strap 72 can extend around rear end 60 for providing support, for example, in supporting a patient with foot drop. Support strap 72 can include coupling portion 77 at one end thereof. Coupling portion 77 can be formed of a hook and loop material. Coupling portion 77 can attach to attachment section 58.

Figure 16:
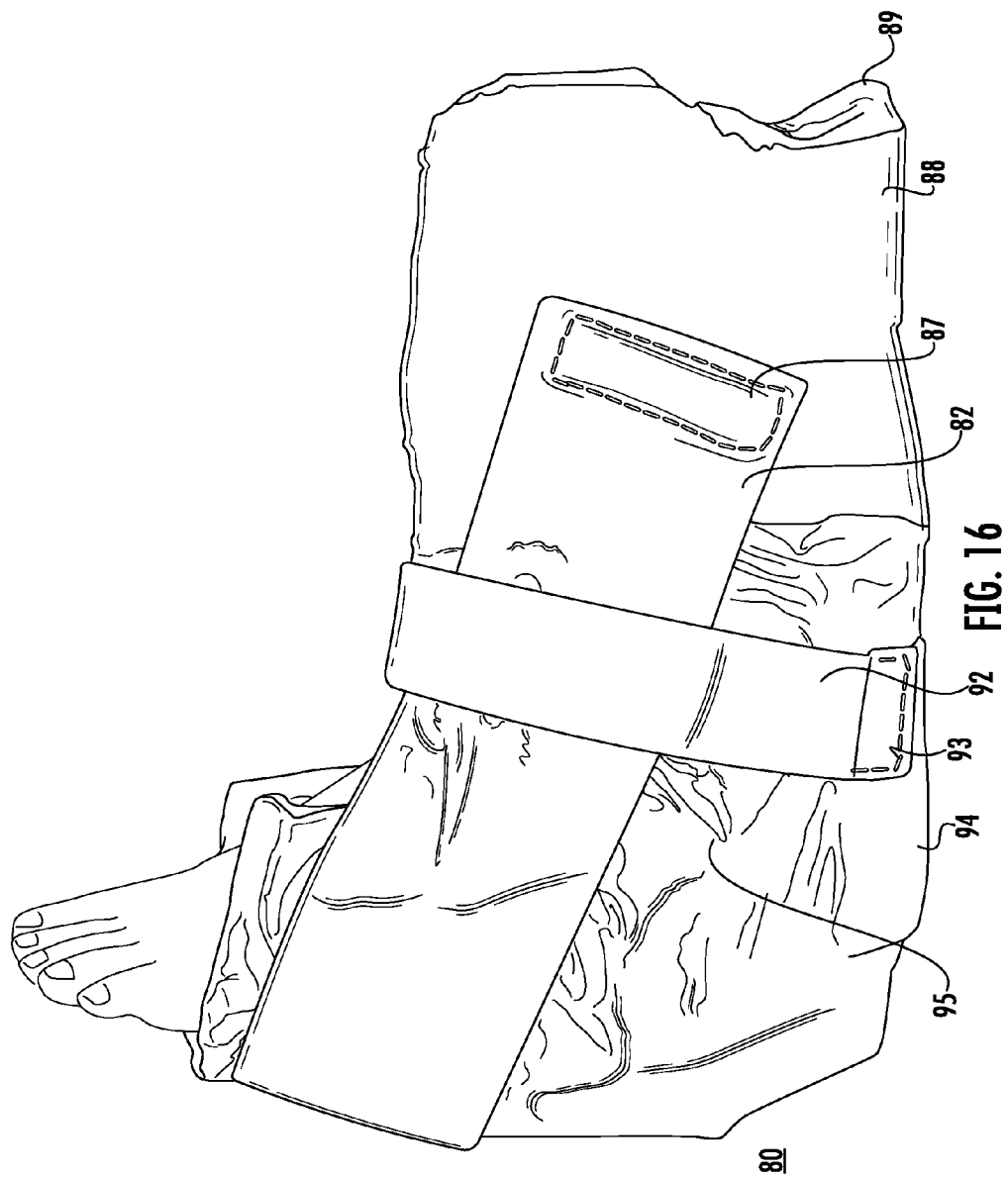
FIG. 16 is a schematic diagram of an alternate embodiment of a fluidized lower leg protection and support system including an outer support, support strap and anide strap.
Figure 17:
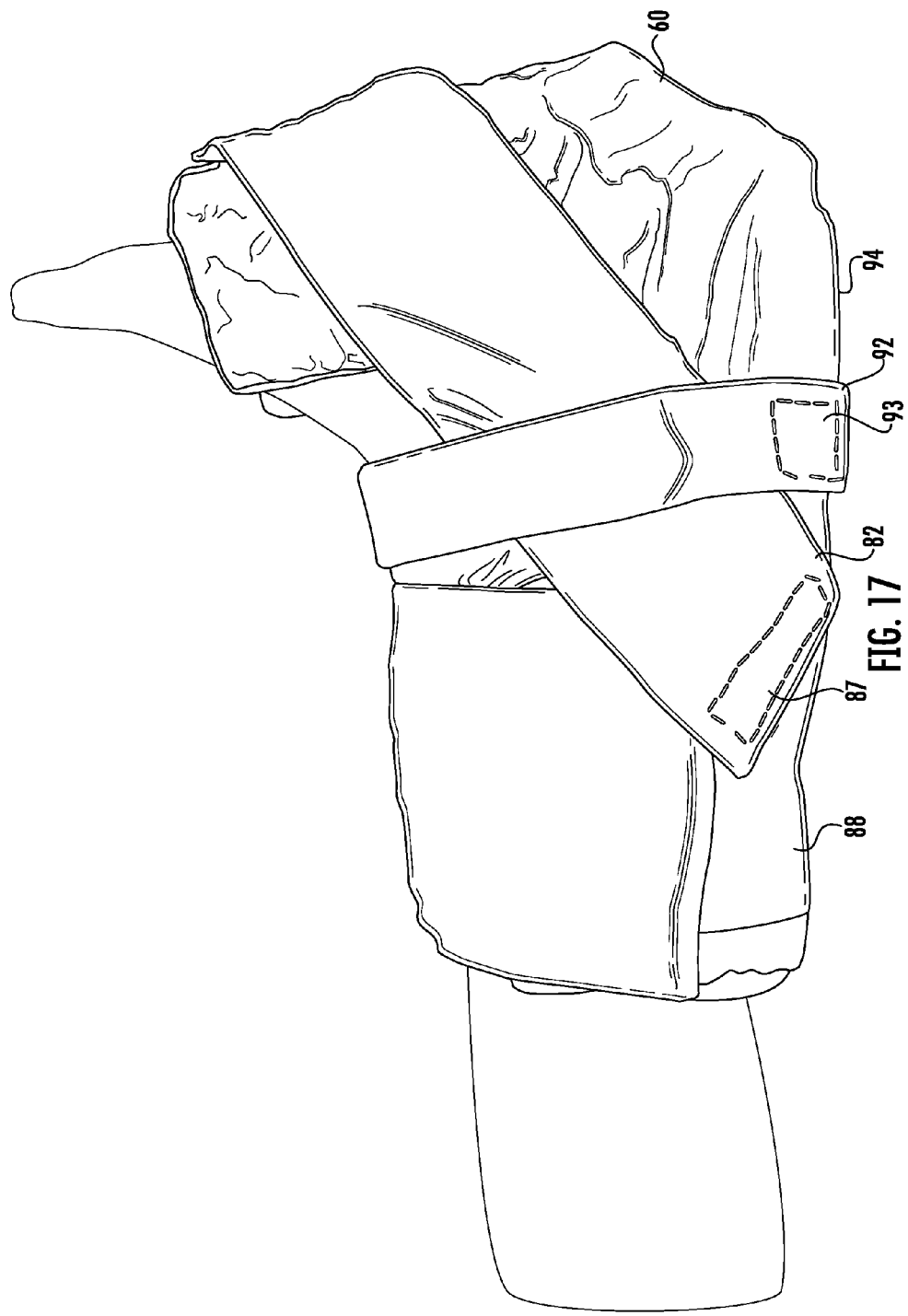
FIG. 17 is a schematic diagram of the embodiment of a fluidized lower leg protection and support system shown in FIG. 16 from an opposite side.

FIGS. 16 and 17 illustrate an alternate embodiment of a fluidized lower leg protection support system 80. Support strap 82 can include coupling portion 87 at one end thereof. Coupling portion 87 can be formed of a hook and loop material. Coupling portion 87 can attach to attachment section 88. Attachment section 88 can be positioned circumferentially around top portion 89. Coupling portion 87 can be coupled at various locations on attachment section 88. Ankle strap 92 can attach to attachment section 94. Ankle strap 92 can include coupling portion 93 at one end thereof. Coupling portion 93 can be formed of a hook and loop material. Attachment section 94 can be formed of a hook and loop material. Ankle strap 92 can be positioned above ankle 95. Attachment section 94 can be positioned adjacent or below ankle 95.

Figure 18:
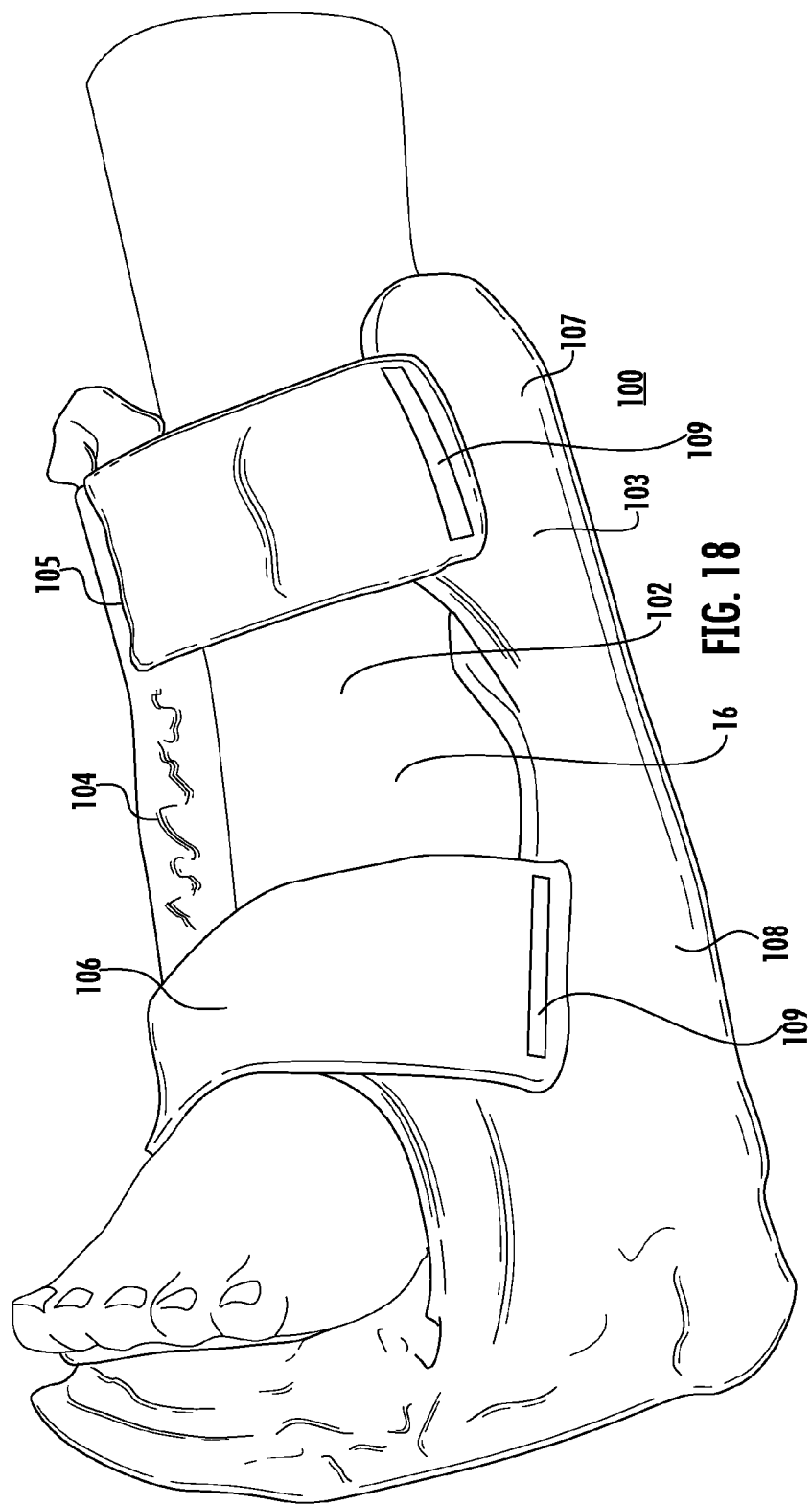
FIG. 18 is a schematic diagram of an alternate embodiment of a fluidized lower leg protection and support system including an opening between side portions of the outer support.

FIG. 18 illustrates an alternate embodiment of a fluidized lower leg protection and support system 100 which includes opening 102 between side portions 103 and 104 for allowing air to contact lower leg 16 and allowing cooling of lower leg 16 while providing support. Straps 105 and 106 can attach to respective attachment sections 107 and 108. Straps 105 and 106 can include coupling portion 109 at one end thereof. Coupling portion 109 can be formed of a hook and loop material. Attachment section 107 and 108 can be formed of a hook and loop material.

Inner positioner 14 described above can be used with each of the fluidized lower leg protection support systems 50, 70, 80 and 100. In one embodiment, inner positioner 14 is positioned horizontally at ankle 19 and wraps around the Achilles to protect the ankle.

FIG. 19 illustrates an alternate embodiment of fluidized lower leg support system 1000. Outer support 1001 of system 1000 has a three layer construction. Top layer 1020, intermediate layer 1030 and bottom layer 1040 are sealed to one another along outside edge 1050. For example, top layer 1020, intermediate layer 1030 and bottom layer 1040 can be formed of urethane.

Plenum 1100 formed between top layer 1020 and intermediate layer 1030 can include dynamic air. Air 1150 is pumped into plenum 1100 through valve 1110 by pump 1120. Air 1150 is pumped beneath top layer 1020. Top layer 1020 is perforated with apertures 1180. Plenum 1100 provides a dynamic amount of air to system 1000 for adjusting the amount of air in plenum 1140 and providing low air loss.

Plenum 1140 formed between bottom layer 1040 and intermediate layer 1030 can include a fixed amount of static air. In one embodiment, plenum 1140 is filled with an ultra low pressure of a pressure of about 20 mm of water to about 5 mm of water or in some cases even lower pressures can be used. Valve 1160 can be used to adjust the pressure in plenum 1140.

FIGS. 20-21 illustrate an alternate embodiment of fluidized lower leg support system 2000. Outer support 2052 can include a plurality of rows of parallel ultra low pressure plenums 2053. For example, ultra low pressure plenums 2053 can be positioned within outer support 2052 along the length $L_1$ of outer support 2052.

Cover 2100 can be attached over outer support 2052 after lower leg 16 is received in outer support 2052 as shown in FIG. 21A. Rear end 2060 of cover 2100 can include overlapping flap members 2062 and 2063. Flap members 2062 and 2063 can include respective coupling portions 2064 and 2065 for attaching flap members 2062 and 2063 to one another. For example, coupling portions 2064 and 2065 can be formed of a hook and loop material. Strap 2056 can be adjustable for closing cover 2100 for different sizes of legs. Strap 2056 can include a coupling portion 2057 at one end thereof for attaching to attachment section 2058. Coupling portion 2057 can be formed of a hook and loop material. Attachment section 2058 can be formed of a hook and loop material. Attachment section 2058 can be positioned along length $L_1$ of cover 2100.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A support system for a body part comprising:
an inner positioner, said inner positioner comprises a bladder filled with a fluidized particulate material, said inner positioner can retain its shape after sculpting, said inner positioner adapted to provide three dimensional contouring of the received body part; and
an outer support comprising an ultra low pressure plenum including a gas therein, wherein said inner positioner is received over said outer support and displaces said gas within said plenum of said outer support, wherein said pressure within said bladder of said inner positioner has a pressure of less than about 500 millibars to about 5 millibars.

2. The support system of claim 1 wherein said pressure within said bladder of said inner positioner has a pressure of less than about 350 millibars to about 5 millibars.

3. The support system of claim 1 wherein said fluidized material is selected from the group comprising beads, polyethylene beads, polystyrene (PS) beads, expanded polyethylene (PE), crosslinked expanded polyethylene (PE), polypropylene (PP) pellets, closed cell foams cut into a plurality of shapes, microspheres, and encapsulated phase changing materials (PCM).

4. The support system of claim 1 wherein said outer support comprises a plurality of the ultra low pressure plenums.

5. The support system of claim 1 wherein said inner positioner covers an area of less than about 30% of said outer support and a pressure in said ultra low pressure plenum is less than about 20 mm of water.

6. The support system of claim 1 wherein said inner positioner covers an area of between about 30% and about 60% of said outer support and a pressure in said ultra low pressure plenum is less than about 10 mm of water.

7. The support system of claim 1 wherein said inner positioner covers an area of greater than about 60% of said outer support and a pressure in said ultra low pressure plenum is less than about 5 mm of water.

8. A support system for a body part comprising:
an inner positioner, said inner positioner adapted to provide three dimensional contouring of the received body part; and
an outer support comprising an ultra low pressure plenum including a gas therein, wherein said inner positioner displaces said gas within said plenum wherein said outer support has an opening in a front portion and further comprises a flap for closing the opening.

9. A support system for a body part comprising:
an inner positioner, said inner positioner adapted to provide three dimensional contouring of the received body part; and
an outer support comprising an ultra low pressure plenum including a gas therein, wherein said inner positioner displaces said gas within said plenum wherein a rear end of said outer support includes overlapping flap members, each of said flap members including a coupling portion, said coupling portions attaching said flap members to one another, wherein said flap members are adapted to be opened to provide access to a foot received in the support system.

10. The support system of claim 9 wherein the coupling portions are formed of a hook and loop material.

11. The support system of claim 9 further comprising a support strap, said support strap extending from each side of said outer support around the rear end of said outer support.

12. The support system of claim 11 wherein said support strap includes a coupling portion at one end thereof, said coupling portion of said support strap being coupled to a attachment section of said outer support.

13. The support system of claim 12 wherein the coupling portion of said strap is formed of a hook and loop material.

14. The support system of claim 11 further comprising an ankle strap, said ankle strap including a coupling portion at one end thereof, the coupling portion of the ankle strap being coupled to an attachment section of said outer support.

15. The support system of claim 14 wherein the coupling portion of said ankle strap is formed of a hook and loop material.

16. A support system for a body part comprising:

an inner positioner, said inner positioner adapted to provide three dimensional contouring of the received body part; and an outer support comprising an ultra low pressure plenum including a gas therein, wherein said inner positioner displaces said gas within said plenum wherein said outer support includes an opening between side portions, one or more straps being attached to attachment portions of said side portions, said straps extending over said opening, wherein said opening is adapted to allow air to contact a lower leg received in said outer support.

17. A support system for a body part comprising:

an inner positioner, said inner positioner adapted to provide three dimensional contouring of the received body part;

an outer support comprising an ultra low pressure plenum including a gas therein, wherein said inner positioner displaces said gas within said plenum and a cover positioned over the outer support, a rear of said cover includes overlapping flap members, each of said flap members including a coupling portion, said coupling portions attaching said flap members to one another, wherein said flap members are adapted to be opened to provide access to a foot received in the support system.

18. A method of supporting a body part comprising the steps of:

providing a body a support system for a body part, said support system comprising an inner positioner, said inner positioner adapted to provide three dimensional contouring of the received body part; an outer positioner comprising an ultra low pressure plenum including a gas therein, said outer support has an opening in a front portion a flap for closing the opening;

opening said flap;

placing said body part over said inner positioner and closing said flap, wherein said inner positioner displaces said gas within said plenum.

19. The method of claim 18 wherein said flap including a first coupling portion for coupling the flap to a second coupling portion of the outer support, said first and second coupling portions closing said flap to said outer support.

20. The method of claim 18 wherein said inner positioner comprises a bladder filled with a fluidized particulate material.

21. The method of claim 18 wherein said pressure within said bladder of said inner positioner has a pressure of less than about 500 millibars.

22. The method of claim 18 wherein said fluidized material is selected from the group comprising beads, polyethylene beads, polystyrene (PS) beads, expanded polyethylene (PE), crosslinked expanded polyethylene (PE), polypropylene (PP) pellets, closed cell foams, microspheres, encapsulated phase changing materials (PCM).

23. A support system for a body part comprising:

an inner positioner, said inner positioner adapted to provide three dimensional contouring of the received body part; and an outer support comprising a top layer, intermediate layer and bottom layer sealed to one another along respective edges, a first plenum formed between the top layer and the intermediate layer, said first plenum includes perforations and further comprising a valve connected to the first plenum and a pump, the pump providing a dynamic amount of air through said valve to the first plenum; and a second plenum formed between the bottom layer and the intermediate layer, said second plenum including a fixed amount of static air.

* * * * *